(12) United States Patent
Ertl

(10) Patent No.: US 10,253,340 B2
(45) Date of Patent: *Apr. 9, 2019

(54) METHOD FOR THE ISOMERISATION OF GLUCOSE

(71) Applicant: ANNIKKI GMBH, Graz (AT)

(72) Inventor: Ortwin Ertl, Vasoldsberg (AT)

(73) Assignee: ANNIKKI GMBH, Graz (AT)

( * ) Notice: Subject to any disclaimer, the term of this patent is extended or adjusted under 35 U.S.C. 154(b) by 649 days.

This patent is subject to a terminal disclaimer.

(21) Appl. No.: 14/779,543

(22) PCT Filed: Mar. 25, 2014

(86) PCT No.: PCT/EP2014/055936
§ 371 (c)(1),
(2) Date: Sep. 23, 2015

(87) PCT Pub. No.: WO2014/154676
PCT Pub. Date: Oct. 2, 2014

(65) Prior Publication Data
US 2016/0053289 A1 Feb. 25, 2016

(30) Foreign Application Priority Data
Mar. 27, 2013 (AT) .............. A 50210/2013

(51) Int. Cl.
| | | |
|---|---|---|
| C12P 19/02 | (2006.01) | |
| C12P 19/24 | (2006.01) | |
| C07D 307/46 | (2006.01) | |
| C07D 307/58 | (2006.01) | |
| A61K 38/00 | (2006.01) | |

(52) U.S. Cl.
CPC ............ *C12P 19/02* (2013.01); *C07D 307/46* (2013.01); *C07D 307/58* (2013.01); *C12Y 101/01014* (2013.01); *C12Y 101/01307* (2013.01); *C12Y 101/01001* (2013.01); *C12Y 106/01* (2013.01)

(58) Field of Classification Search
None
See application file for complete search history.

(56) References Cited

U.S. PATENT DOCUMENTS

| | | | |
|---|---|---|---|
| 2,950,228 A | 8/1960 | Marshall | |
| 3,616,221 A | 10/1971 | Takasaki et al. | |
| 3,868,304 A | 2/1975 | Messing | |
| 4,467,033 A | 8/1984 | Horwath et al. | |
| 4,895,601 A | 1/1990 | Binder et al. | |
| 5,047,088 A | 9/1991 | Liaw et al. | |
| 5,221,478 A | 1/1993 | Dhingra et al. | |
| 7,053,188 B2* | 5/2006 | Morre .................. | C07K 16/30 530/388.1 |
| 7,163,815 B2 | 1/2007 | Riebel-Bommarius et al. | |
| 2004/0231662 A1* | 11/2004 | De Mendonca Ferreira ............... | C13B 20/14 127/36 |
| 2006/0035353 A1 | 2/2006 | Zhao et al. | |
| 2011/0207923 A1* | 8/2011 | Moliner-Marin .... | C07D 307/58 536/125 |
| 2014/0377798 A1* | 12/2014 | Ertl .......................... | C12P 19/02 435/52 |

FOREIGN PATENT DOCUMENTS

| | | |
|---|---|---|
| DE | 3326546 | 7/1985 |
| DE | 10247147 | 4/2004 |
| DE | 60006330 | 8/2004 |
| DE | 69839381 | 4/2009 |
| EP | 1078983 | 2/2001 |
| EP | 1152054 | 11/2001 |
| EP | 1285962 | 2/2003 |

(Continued)

OTHER PUBLICATIONS

Sigma (2018) http://www.chemspider.com/Chemical-Structure.12814.html, pp. 1-3.*
Findrik et al., "Coenzyme regeneration catalyzed by NADH oxidase from *Lactobacillus brevis* in the reaction of L-amino acid oxidation", Biochemical Engineering Journal 39 (2008) 319-327.
Harvey et al., "Chapter 12: Metabolism of Monosaccharides and Disaccharides, Lippincott's Illustrated Reviews: Biochemistry (Fifth Edition)", Jan. 1, 2011, Wolters Kluwer, Lippincott Williams & Wilkins, Baltimore MD 21201, USA.
Hummel et al., "An Efficient and Selective Enzymatic Oxidation System for the Synthesis of Enantiomerically Pure D-tert-Leucine", Org. Lett., 2003, 5 (20), pp. 3649-3650.
Ikemi et al., "Sorbitol production in charged membrane bioreactor with coenzyme regeneration system. I. Selective retainment of NADP(H) in a continuous reaction", Biotechnology and Bioengineering, Wiley & Sons, Hoboken, NJ, US, vol. 36, No. 2, Jun. 20, 1990, p. 149-154, XP002360459.

(Continued)

*Primary Examiner* — Manjunath N Rao
*Assistant Examiner* — Samuel W Liu
(74) *Attorney, Agent, or Firm* — Workman Nydegger

(57) ABSTRACT

Disclosed is a method for the isomerization of glucose by reduction to sorbitol and subsequent oxidation to fructose, in which the redox cofactors $NAD^+$/NADH and $NADP^+$/NADPH are regenerated in a one-pot-reaction, wherein one of the two redox cofactors is obtained in the reduced form thereof and the other redox cofactor in the oxidized form thereof as a result of at least two additional enzymatically catalyzed redox reactions (product forming reactions) taking place in the same reaction batch, wherein a) in the regeneration reaction, which transfers the reduced cofactor back to its originally oxidized form, oxygen or a compound of the general formula $R_1C(O)COOH$ is reduced, and b) in the regeneration reaction, which transfers the oxidized cofactor back to its originally reduced form, a compound of the general formula $R_2CH(OH)R_3$ is oxidized, wherein $R_1$, $R_2$ and $R_3$ have different meanings in the compounds, characterized in that a mixture of glucose and fructose is used as a starting material. Furthermore, the use of fructose thus produced in a method for producing furan derivatives is disclosed.

22 Claims, No Drawings

(56) References Cited

FOREIGN PATENT DOCUMENTS

| JP | 2003159093 | 6/2003 |
|----|------------|--------|
| WO | WO8604353 | 7/1986 |
| WO | WO2006002021 | 1/2006 |
| WO | WO2009121785 | 10/2009 |
| WO | WO2011124639 | 10/2011 |
| WO | WO2012015616 | 2/2012 |
| WO | WO2013117584 | 8/2013 |
| WO | WO2013117585 | 8/2013 |

OTHER PUBLICATIONS

Ng et al., "Sorbitol dehydrogenase from Bacillus subtilis: Purification, characterization, and gene cloning", Journal of Biological Chemistry, American Society for Biochemistry and Molecular Biology, US, vol. 267, No. 35, Jan. 1, 1992, p. 24989-24994, XP002151857.

Schrittwieser et al., "Recent biocatalytic oxidationreduction cascades", Current Opinion in Chemical Biology, vol. 15, No. 2, Apr. 1, 2011, p. 249-256, XP028187359.

Shih et al., "Preparation of Functionalized Imidazolium Salts under Microwave Irridiation", Synthetic Communications, vol. 36, Issue 14, Jun. 2006, pp. 2059-2067.

Voss et al., "Orchestration of Concurrent Oxidation and Reduction Cycles for Steroinversion and Deracemisation of sec-Alcohols", JACS Articles, 2008, 130, 13969-13972.

Wang et al., "Heterologous expression, purification, and characterization of xylose reductase from *Candida shehatae*", Biotechnol. Lett., 2007, vol. 29, p. 1409-1412.

Woodyer et al., "Mechanistic investigation of a highly active phosphite dehydrogenase mutant and its application for NADPH regeneration", FEBS J., 2005, vol. 272, p. 3816-3827.

* cited by examiner

METHOD FOR THE ISOMERISATION OF GLUCOSE

The present invention relates to a method for the isomerisation of glucose and for the enrichment of fructose in a mixture of fructose and glucose.

D-glucose is present in large amounts in various biopolymers, which are part of renewable raw materials. Examples thereof are starch (e.g. corn starch) or cellulose (e.g. of lignocellulosic biomass).

A common possibility for converting D-glucose to D-fructose proceeds by use of an appropriate D-glucose isomerase, e.g. D-xylose isomerase, which accepts D-glucose as substrate. Such methods have been known for a long time, e.g. from U.S. Pat. No. 2,950,228, and also been suitable for industrial use, as for example described in U.S. Pat. No. 3,616,221 or U.S. Pat. No. 3,868,304.

One problem herewith is that in general a maximum of approximately 42% of D-glucose can be converted to D-fructose. Further enrichment of D-fructose vs. D-glucose is only achievable through separation methods. One possibility herefore is the use of chromatographic methods, as for example described in U.S. Pat. No. 5,221,478. The food sector often seeks only a partial enrichment of D-fructose. In particular, chromatographic methods for producing relatively pure to highly pure D-fructose are rather laborious.

In addition to the use of isomerases, the literature also describes enzymatic redox reactions on carbohydrates.

For example, DE69839381 describes a sorbitol dehydrogenase that is used for converting D-sorbitol to L-sorbitol and may be used for the production of ascorbic acid.

DE10247147 describes a method in which D-fructose is reduced to D-mannitol by use of D-mannitol-2-dehydrogenase.

U.S. Pat. No. 4,467,033 describes the enzymatic oxidation of L-sorbitol to L-fructose.

Examples for the reduction of D-xylose to xylitol are, for example, disclosed in US20060035353 or in Woodyer R. et al., FEBS J., 2005, Volume 272, p. 3816-3827.

It has been shown that suitable xylose reductases may be used to reduce D-glucose to D-sorbitol (e.g. Wang X. et al., Biotechnol. Lett., 2007, Volume 29, p. 1409-1412).

Sugar redox enzymes, such as sorbitol dehydrogenase, are also used for diagnostic purposes (e.g. DE60006330).

These methods are individual redox reactions, in which either a reduction or an oxidation takes place for the formation of each product. In industrial processes, enzyme-catalysed redox reactions are, for example, used in the production of chiral alcohols, α-amino acids, and α-hydroxy acids. The industrial processes known so far have usually used a redox enzyme for product synthesis, and optionally another enzyme for the regeneration of a cofactor. In contrast thereto are methods in which two or more enzymatic redox reactions involved in the product formation as well as any enzymatic reactions necessary for cofactor regeneration are (simultaneously or sequentially) carried out in one reaction batch, without isolating any intermediate. Recently, such enzymatic cascade reactions—here referred to as one-pot reactions—have attracted significant attention because they effectively reduce operation costs, operation times and environmental impacts. In addition, enzymatic cascades of redox reactions allow transformations that cannot easily be implemented by means of classic chemical methods.

An attempt was described, in which the deracemisation of racemates of secondary alcohols was to be achieved via a prochiral ketone as intermediate and by use of a one-pot system (J. Am. Chem. Soc., 2008, Volume 130, p. 13969-13972). Deracemisation of secondary alcohols was achieved through two alcohol dehydrogenases (S- and R-specific) with different cofactor specificities. A disadvantage of this method is the very low concentration of the substrate used of 0.2-0.5%, which is not suitable for industrial purposes.

Another one-pot system was described in WO 2009/121785, wherein a stereoisomer of an optically active secondary alcohol was oxidised to a ketone and then reduced to the corresponding optical antipode, and wherein two alcohol dehydrogenases with opposite stereoselectivities and different cofactor specificities were used. The cofactors were regenerated by means of a so-called "hybrid transfer system" by use of only one additional enzyme. In order to regenerate the cofactors, different enzymes were used, such as formate dehydrogenase, glucose dehydrogenase, lactate dehydrogenase. A disadvantage of this method is the low concentration of the substrates used.

In contrast thereto, numerous individual enzymatic redox reactions are known. One exemplary application of the production of chiral hydroxy compounds is based on corresponding prochiral keto compounds. In this method, the cofactor is regenerated via an additional enzyme. All these methods have in common that they represent isolated reduction reactions and regenerate NAD(P)H (see e.g. EP1152054).

Further examples of an enzymatic production of chiral, enantiomer-enriched, organic compounds, such as alcohols or amino acids, have been described (Organic Letters, 2003, Volume 5, p. 3649-3650; U.S. Pat. No. 7,163,815; Biochem. Eng. J., 2008, Volume 39(2) p. 319-327; EP1285962). In these systems, an NAD(P)H-dependent oxidase from *Lactobacillus brevis* or *Lactobacillus sanfranciscensis* was used as cofactor regeneration enzyme. These attempts also represent individual reactions for product forming.

The oxidation or reduction reactions proceeding separately as mentioned above lack the advantages of one-pot reactions, such as efficiency via reduced time and materials.

Isolating fructose from aqueous solutions is, for example, possible according to a method described in U.S. Pat. No. 4,895,601 or U.S. Pat. No. 5,047,088.

All processes known until today have different disadvantages, for example low initial concentrations of the substrate, low overall yields.

Surprisingly, a possibility of achieving higher enrichment of fructose during isomerisation of glucose to fructose has now been found.

In one aspect, the present invention provides a method for the isomerisation of glucose by reduction to sorbitol and subsequent oxidation to fructose, in which the redox cofactors NAD+/NADH and NADP+/NADPH are regenerated in a one-pot reaction, and wherein one of the two redox cofactors is obtained in the reduced form thereof while the other one is obtained in the oxidised form thereof as a result of at least two additional enzymatically catalysed redox reactions (product forming reactions) taking place in the same reaction batch wherein a) in the regeneration reaction, which transfers the reduced cofactor back to its originally oxidised form, oxygen or a compound of the general formula

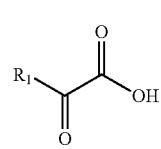

I wherein $R_1$ is a straight or branched $(C_{1-4})$-alkyl group or a $(C_{1-4})$-carboxyalkyl group, is reduced, and b) in the regeneration reaction, which transfers the oxidised cofactor back to its originally reduced form, a $(C_{4-8})$ cycloalkanol or a compound of the general formula

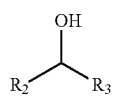

II wherein $R_2$ and $R_3$ are each independently selected from the group consisting of H, $(C_1\text{-}6)$alkyl, wherein alkyl is straight or branched, $(C_{2-6})$alkenyl, wherein alkenyl is straight or branched and contains one to three double bonds, aryl, in particular $(C_{6-12})$aryl, carboxyl, or $(C_{1-4})$carboxyalkyl, in particular also cycloalkyl, e.g. $(C_{3-8})$cycloalkyl, is oxidised, characterised in that a mixture of glucose and fructose is used as a starting material.

A method provided according to the present invention is herein also referred to as "method according to (of) the present invention."

In a further aspect, the present invention provides a method according to the present invention, wherein in a) a compound of the general formula I, wherein $R_1$ is a substituted or unsubstituted $(C_{1-4})$alkyl group, is reduced, and in b) a compound of the general formula II, wherein $R_2$ and $R_3$ are independently selected for the group consisting of H, $(C_{1-6})$alkyl, wherein alkyl is straight or branched, $(C_{2-6})$ alkenyl, wherein alkenyl is straight or branched and optionally contains up to three double bonds, cycloalkyl, in particular $(C_{3-8})$cycloalkyl, aryl, in particular $(C_{6-12})$aryl, $(C_{1-4})$carboxyalkyl, if compound I is a pyruvate, optionally also carboxyl, is oxidised.

In a further aspect, $R_2$ and $R_3$ in a method according to the present invention are independently selected from the group consisting of H, $(C_{1-6})$alkyl, wherein alkyl is straight or branched, $(C_{2-6})$alkenyl, wherein alkenyl is straight or branched and contains one to three double bonds, aryl, in particular $(C_{6-12})$aryl, carboxyl or $(C_{1-4})$carboxyalkyl.

In a particular aspect, the reaction according to the present invention proceeds according to reaction scheme 1 below:

Reaction scheme 1

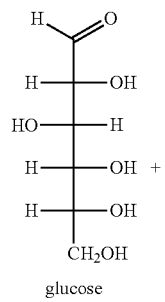

glucose

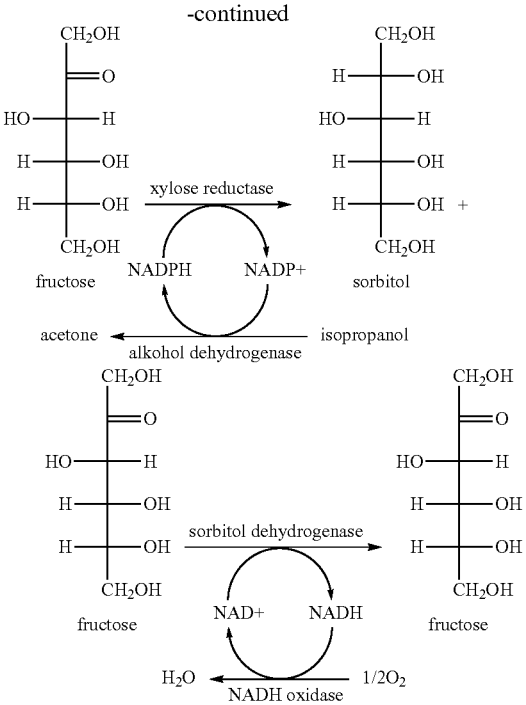

Compared to the state of the art, a method according to the present invention represents a significant improvement of methods in which compounds are oxidised and reduced enzymatically because it allows for the necessary oxidation and reduction reactions as well as the corresponding reactions for cofactor regeneration in one reaction batch and at the same time the use of significantly higher substrate concentrations than according to the state of the art.

In a method according to the present invention, the cofactors NADH and NADPH are used. Here, $NAD^+$ represents the oxidised form and NADH the reduced form of nicotinamide adenine dinucleotide, while $NADP^+$ represents the oxidised form and NADPH the reduced form of nicotinamide adenine dinucleotide phosphate.

Herein, the terms "oxidation reaction(s)" and "reduction reaction(s)" represent those enzyme-catalysed redox reactions that are not part of cofactor regeneration and are, in a method according to the present invention, involved in forming the product. "Oxidation reaction(s)" and "reduction reaction(s)" are collectively referred to as "product forming reactions". The product forming reactions in a method according to the present invention each comprise at least one oxidation reaction and at least one reduction reaction.

If $NAD^+$ is used as a cofactor for the oxidation reaction(s), NADPH is the cofactor for the reduction reaction(s). If $NADP^+$ is used as a cofactor for the oxidation reaction(s), NADH is the cofactor for the reduction reaction(s).

In a method according to the present invention, (an) oxidation reaction(s) and (a) reduction reaction(s) may be carried out parallel in time or non-parallel in time, i.e. sequentially, in the same reaction batch.

Herein, substrate refers to those compounds that are used with the aim of forming a product. Herein, cosubstrates refer to those compounds that are converted during cofactor regeneration.

In a method according to the present invention several substrates, namely glucose and sorbitol, are used. Here, (a) reduction and/or oxidation reaction(s) take place at the same substrate (molecular skeleton). In addition, in a method according to the present invention reduction and oxidation reactions take place at two different functional groups at different positions in the molecular skeleton.

Herein, a "one-pot reaction" refers to a method in which two or more redox reactions involved in product formation and two enzymatic systems for cofactor regeneration take place in one reaction batch without isolation of an intermediate.

Mention of an acid or a salt of an acid herein includes the respective other term that is not stated. Also, mention of acids herein includes all esters derived therefrom. In addition, compounds (partially) provided with protective groups are included in the mention of the underlying substance.

In a preferred embodiment of the present in invention, a method according to the present invention is characterised in that an oxidation reaction and a reduction reaction take place parallel in time.

In a preferred embodiment of the present invention, a method according to the present invention is characterised in that an oxidation reaction and a reduction reaction take place at the same molecular skeleton.

In a preferred embodiment of the present invention, a method according to the present invention is characterised in that (secondary alcohol) 2-propanol (isopropyl alcohol, IPA) (cosubstrate) is used as compound of formula II, which is oxidised to acetone by means of an alcohol dehydrogenase, which means that in the regeneration reaction, which transfers the oxidised cofactor $NAD(P)^+$ back to its originally reduced form $NAD(P)H$, 2-propanol is oxidised to acetone by means of an alcohol dehydrogenase.

In a preferred embodiment of the present invention, a method according to the present invention is characterised in that in the regeneration reaction, which transfers the reduced cofactor $NAD(P)H$ back to its originally oxidised form $NAD(P)^+$, oxygen is reduced to water by means of an NADH oxidase.

A method according to the present invention is preferably carried out in an aqueous system.

In a particular embodiment, a method according to the present invention is characterised in that fructose is present in the reaction batch as a substrate with a concentration of at least 5% (w/v) or more, preferably 7% (w/v) or more, most preferably 9% (w/v) or more, e.g. 5% (w/v) to 20% (w/v), such as 5% (w/v) to 15% (w/v), e.g. 5% (w/v) to 12% (w/v), such as 5% (w/v) to 10% (w/v).

In a particular embodiment, a method according to the present invention is characterised in that during the product forming reactions a total turnover of >70%, in particular >90%, is achieved.

In a method according to the present invention, a buffer may be added to the aqueous system. Suitable buffers are, for example, potassium phosphate, Tris HCl and glycine with a pH value of 5 to 10, preferably 6 to 9. In addition or alternatively ions may added to the system for stabilizing the enzymes, such as $Mg^{2+}$, or other additives, such as glycerol. In a method according to the present invention, the added concentration of the cofactors $NAD(P)^+$ and $NAD(P)H$ usually ranges between 0.001 mM and 10 mM, preferably between 0.01 mM and 1 mM.

Depending on the enzymes used, the method according to the present invention may be performed at a temperature of 10° C. to 70° C., preferably 20° C. to 45° C.

In a method according to the present invention, enzymes may be used as such, optionally in the form of cell lysates, optionally as recombinant overexpressed proteins, for example as proteins recombinantly overexpressed in *E. coli*, wherein the corresponding cell lysates may preferably be used without further purification. Depending on the enzyme to be produced, other microorganisms may also be used for expression, e.g. microorganisms known to the skilled person. Integral parts of the respective microorganisms may be either separated in a method according to the invention or used in the reaction as well (e.g. whole-cell biocatalysts). Culture supernatants or lysates of microorganisms that already have sufficient enzymatic activities without recombinant DNA technologies may also be used. In a method according to the invention, enzymes and redox cofactors may either be used in a soluble form or immobilised to solids. Here, the enzyme unit 1 U corresponds to the amount of enzyme that is necessary to convert 1 μmol substrate per min.

In a method according to the present invention, enzymes are preferably used as proteins recombinantly overexpressed in *E. coli*, wherein the corresponding cell lysates are more preferably used without further purification.

Possible enzymes are especially those enzymes that reduce glucose to sorbitol, those that reduce sorbitol to fructose, and those that are able to reduce NADH or NADPH or oxidise NAD or $NADP^+$.

Enzymes that are able to convert glucose to sorbitol include e.g. aldose reductase, such as xylose reductase. An appropriate xylose reductase can, for example, be obtained from *Candida tropicalis*.

Enzymes that are able to convert sorbitol to fructose include e.g. sorbitol dehydrogenases. Suitable sorbitol dehydrogenases can, for example, be obtained from sheep liver, *Bacillus subtilis*, or *Malus domestica*.

Aldose reductases oxidise the redox cofactors $NAD(P)H$ to $NAD(P)^+$ concurrently with the reduction of glucose. Sorbitol dehydrogenases reduce the redox cofactors $NAD(P)^+$ to $NAD(P)H$ concurrently with the oxidation of sorbitol.

For regenerating the redox cofactors $NAD(P)H$ and $NAD(P)^+$ dehydrogenases, such as alcohol dehydrogenases, lactate dehydrogenases, or oxidases, in particular $NAD(P)H$ oxidases, may be used.

Suitable alcohol dehydrogenases can, for example, be obtained from *Lactobacillus kefir*. Suitable lactate dehydrogenases can, for example, be obtained from *Oryctolagus cuniculus*. Suitable NADH oxidases can, for example, be obtained from *Leuconostoc mesenteroides, Streptococcus mutans, Clostridium aminovalericum*.

The starting material in a method according to the present invention is a mixture of glucose and fructose, preferably D-glucose and D-fructose. Such a mixture may be produced in different ways.

For example, glucose may be used as a starting material and be partly isomerised to fructose. Isomerisation can be achieved with known methods, for example by use of ion-exchange resins as homogeneous acid catalysts, or enzymatically, such as by aid of e.g. immobilised isomerase, such as glucose isomerase, e.g. xylose isomerase from *Streptomyces murinus*.

Preferably, a mixture of glucose and fructose is produced from glucose by use of an immobilised glucose isomerase.

Isomerisation of glucose is an equilibrium reaction, wherein the chemical equilibrium between glucose and fructose during the enzymatic reaction is temperature-dependent. So far, the maximum value found in the literature has been, depending on the source, 55% to 58.9% of fructose in the mixture. However, the optimised technical process currently uses a value of approximately 42% due to lower enzyme amounts and shorter reaction times. Higher values have up to now only been possible with higher temperatures. However, isomerisations in 90% of acetone have also been described. Here, up to 60% of fructose conversion may be achieved. But the enzymes required herefore are not very stable under these reaction conditions.

In contrast, the two redox reactions for converting fructose via sorbitol to glucose according to the present invention have been pushed very far towards products by means of suitable cofactor recycling systems.

The starting mixture in a method according to the present invention is preferably a mixture in which the fructose portion amounts to up to 55 wt %, for example 10 wt % to 55 wt %, such as 20 wt % to 50 wt %, e.g. 23 wt % to 45 wt %, such as 25 wt % to 43 wt %.

It has been shown that in stage a) of a method according to the present invention, i.e. the conversion of glucose to sorbitol, at least 80% of the present glucose can be reduced to sorbitol, e.g. at least 90%, in particular at least 95%. For example, 80% to 99.99%, such as 90% to 99.95%, e.g. 95% to 99.9% of the glucose present in the starting mixture can be converted.

In addition, it has been shown that after implementation of stage b) in a method according to the present invention, i.e. after conversion of sorbitol to fructose, a total fructose ratio of all sugars in the mixture of at least 70%, 80%, 90%, 95% or even up to 99.9% can be reached, for example a total fructose ratio of all sugars in the mixture of 60% to 99.99%, e.g. 70% to 99.95%, such as 80% to 99.9%, 90% to 99.8%, even 95% to 99.5% can be reached. In addition, a mixture obtained from a stage b) of a method according to the present invention in which fructose is, for example, already enriched to 60%, may be reused in a method according to the present invention.

Fructose has higher sweetness that glucose, and particularly in the USA sweeteners are produced enzymatically from corn starch, which is practically pure glucose, that are mixtures of glucose and fructose. Such glucose-fructose mixtures include, for example, glucose-fructose syrup (high-fructose corn syrup—HFCS). Corn syrup, for example, is listed as glucose-fructose syrup in the ingredients starting from a content of 5% of fructose on German food products and used as sugar concentrate. If a syrup contains a fraction of fructose higher than 50%, it is correspondingly listed as "fructose-glucose syrup".

By means of a method according to the present invention, such glucose-fructose syrups can be produced without cumbersome separation methods with a desired fructose content of e.g. 60% or more.

In a further aspect, the present invention provides the use of a method according to the present invention for producing a fructose-glucose syrup with a desired fructose content, in particular of 60% and more.

The D-fructose, which can be obtained according to stage a) of the present invention, can e.g. be isolated by means of crystallisation.

A material having a very high D-fructose fraction in the total sugar content is, for example, a suitable starting material for further conversion to furan derivatives.

Converting D-fructose to furan derivatives in stage B) according to the present invention may be carried out according to a suitable method, e.g. a conventional method or as described herein.

Fructose produced according to a method of the present invention may be further converted to furan derivatives.

In a further aspect, the present invention provides a method for obtaining furan derivatives from a mixture of glucose and fructose, characterised in that A) a mixture of glucose and fructose is converted to fructose in an enzymatic method by use and regeneration of redox cofactors, wherein one of the two redox cofactors is obtained in the reduced form thereof while the other redox cofactor is obtained in the oxidised form thereof as a result of at least two additional enzymatically catalysed redox reactions taking place in the same reaction batch, wherein D-glucose is converted to D-fructose with the involvement of two or more oxide reductases, and B) the fructose obtained in A) is converted to furan derivatives.

Herein, a method for obtaining furan derivatives from a mixture of glucose and fructose provided according to the present invention is also referred to as "furan method according to (of) the present invention".

According to conventional methods, conversion of D-fructose to furan derivatives in a furan method according to the present invention can take place in the presence of a catalyst, e.g. an acidic catalyst, such as an inorganic acid, organic acid, e.g. oxalic acid, a zeolite (H form), of transition metal ions, a heterogeneous dissolved metal phosphate, a strongly acidic cation exchanger.

The solvent in a furan method according the present invention may be water or an organic solvent, e.g. dimethyl sulfoxide (DMSO), dimethyl formamide (DMF), N-methyl pyrrolidone; the conversion of D-fructose to furan derivatives in stage B) according to the present invention preferably takes place in the presence of an acidic catalyst and in the presence of N-methyl pyrrolidone (N-methyl-2-pyrrolidone, NMP) of the formula

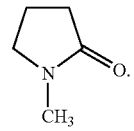

Conversion of D-fructose to furan derivatives in stage B) of a furan method according to the present invention may either be carried out as a batch process or as a continuous process; in a preferred embodiment, stage B) according to the present invention is carried out under microwave heating.

Particular embodiments of the furan method of the present invention are characterised in that the conversion of D-fructose to furan derivatives uses N-methyl-2-pyrrolidone (NMP) either as reaction solvent or as co-solvent, i.e. as additive to another solvent.

In a particular embodiment of a furan method according to the invention, stage B) uses NMP as (co-)solvent, e.g. as reaction solvent or as additive to another solvent.

In a furan method according to the present invention, NMP may, if NMP is used as solvent, be used as only solvent or NMP may be used together with another co-solvent, wherein in case a co-solvent is used, an NMP concentration of up to 70% (v/v), for example up to 60% (v/v), based on the total solvent amount, may be used. Possible co-solvents are e.g. water or an organic solvent, e.g. as they are known from the state of the art, such as N,N-dimethyl sulfoxide (DMSO) or N,N-dimethyl formamide (DMF).

In a furan method according to stage B) of the present invention, D-fructose may be used in an amount of up to 40% (w/v) and is generally used in an amount of 5 to 20%, even though the reaction also takes place at lower concentrations, e.g. at a D-fructose concentration of (approximately) 1% (w/v). The minimum value is rather defined by cost effectiveness and not chemically.

Acidic catalysts in stage B) of a furan method according to the present invention usually include acidic catalysts that may be used in the conversion of fructose to furan derivatives. Preferably, the catalyst is a Brønsted acid.

Here, homogeneous acidic catalysts, e.g. sulphuric acid or hydrochloric acid, or heterogeneous acidic catalysts, e.g. cation exchange resins such as montmorillonites, preferably montmorillonite KSF®, or an AMBERLITE, e.g. Amberlite®, preferably Amberlite 15®, may be used. In addition, Lewis acid catalysts, such as $CrCl_2$, $AlCl_3$, $SiO_2$—$MgCl_2$, or a SILP (silica supported ionic liquid phase) catalyst may be used in a method of the present invention. However, in general results therewith are not as good as those of the above catalysts.

In a further aspect, a furan method of the present invention is characterised in that during the conversion of D-fructose to furan derivatives in stage B) the acidic catalyst used is
a homogeneous acid catalyst, preferably sulphuric acid or hydrochloric acid;
a heterogeneous acidic catalyst, preferably an ion exchanger, e.g. a montmorillonite, such as Montmorillonit KSF®, or an AMBERLITE, such as Amberlite®, preferably Amberlite 15®,
a Lewis acid catalyst, e.g. $CrCl_2$, $AlCl_3$ or $SiO_2$—$MgCl_2$,
a SILP catalyst,
preferably a homogeneous or heterogeneous acidic catalyst.

A skilled person can easily determine the required amount of a catalyst in stage B) through simple preliminary tests. The amount depends on the type of catalyst used.

The following catalyst amounts based on the fructose amounts used are given as examples, in particular for the case that NMP is used as solvent:

| Catalyst | Amount |
| --- | --- |
| 1N HCl | 20 to 200% (v/v) |
| HCl (37%) | 2 to 25% (v/w) |
| 1N $H_2SO_4$ | 20 to 200% (v/w) |
| $H_2SO_4$ conc. | 2 to 25% (v/w) |
| Montmorillonite KSF ® | 1 to 50% (w/w) |
| Amberlite 15 ® | 1 to 50% (w/w) |
| $CrCl_2$, $AlCl_3$ | 1 to 20% (w/w) |
| $SiO_2$—$MgCl_2$ | 20 to 200% (w/w) |
| SILP | 10-200% (w/w) |

At a concentration of approximately 10% (w/v) of D-fructose, the stated values are unproblematic, at higher fructose concentrations the amount of the catalysts has to be limited so that the fructose can still be dissolved in the remaining amount of solvent.

Stage B) of the furan method according to the present invention is carried out at suitable temperatures. Suitable temperatures include, in particular if NMP is used as solvent, temperatures of 100 to 220° C., preferably 115 to 200° C., most preferably 135 to 185° C.

The reactions in stage B) under use of NMP as solvent were carried out in closed vessels (batch, microwave) throughout the experiment, without active pressure control. From the microwave runs, the maximum pressure for NMP may be assumed to be 2-4 bar, depending on the additive. If e.g. HCl is used as catalyst, the developing pressure rises up to 15 bar. In continuous operation, a constant back pressure of up to 40 bar was applied for preventing the solvent from boiling. Pressure either arises as vapour pressure from (a) solvent(s) or additives or a system-related (pumping) pressure is applied. However, the pressure does not seem to be decisive for the reaction mechanism.

It has been found that the main furan derivative developing in a furan method according to the present invention is hydroxy methyl furfural (HMF) of the formula

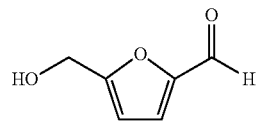

hydroxy methyl furfural (HMF).

In a further aspect, a furan method according to the present invention is characterised in that the furan derivative is hydroxyl methyl furfural.

In a furan method of the present invention, "HMF selectivity" is to be understood to represent the portion of consumed D-fructose that is converted to HMF.

Furan derivatives produced in a furan method of the present invention may be used either directly or be converted to secondary products in further chemical reactions. For example, hydroxyl methyl furfural may be further oxidised to 2,5-furan dicarbonic acid (FDCA) of the formula

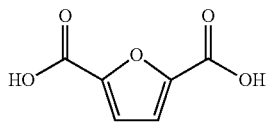

2,5-furan dicarbonic acid (FDCA).

As is known, FDCA can be used as monomer for the production of polymers, such as polyethylene furanoate (PEF), which may be used similarly to polyethylene terephthalate (PET), for example for hollow bodies, in particular bottles, e.g. beverage bottles, bottles for cosmetics, or bottles for cleaning agents. With the simultaneous use of ethylene glycol from regenerative sources and FDCA, which is accessible from HMF, produced in a method according to the present invention, PEF may be obtained, which consists practically completely of renewable raw materials.

In a further aspect, the present invention is characterised in that the furan derivatives produced are further converted, e.g. that hydroxyl methyl furfural is further oxidised to 2,5-furan dicarbonic acid, which is optionally subjected to polymerisation, e.g. for producing polymers, such as polyethylene furanoate (PEF).

EXAMPLE 1

Production of Fructose from Glucose-Fructose Syrup by Glucose Isomerase Followed by a Two-Stage Redox Process 750 mg of D-glucose were dissolved in 50 mM of Tris buffer (pH=8.0 at 25° C.) to a total volume of 5 ml. To this mixture, 250 mg of immobilised glucose isomerase from *Streptomyces murinus* (Sigma-Aldrich, Novozymes Sweetzyme ITC)) were added, and the suspension was gently shaken at 50° C. for 6 h. This led to the conversion of approximately 33% of glucose to fructose. The glucose isomerase was removed by centrifugation (5000 g, 1 min). In a 2 ml glass vessel, 400 μl of the solution were then treated with 10 μl of Tris HCl (0.5 M, pH=8.0), 20 μl of xylose reductase from *Candida tropicalis* (overexpressed in *E. coli* BL21 (DE3), 280 U/ml), 30 μl of alcohol dehydrogenase from *Lactobacillus* kefir (overexpressed in *E. coli* BL21 (DE3), 130 U/ml), and 35 μl of 2-propanol. The reaction was carried out in an open system in which the glass vessel was shaken for 24 h at 40° C. (Eppendorf Thermomix®, 850 rpm). The open system allows the reaction product of acetone to evaporate, which drives the reaction towards sorbitol formation. The following supplementary additions were made: 15 μl of 2-propanol after 4 h, 25 μl of 2-propanol after 18 h, and 50 μl of water after 18 h. 98.5% of the glucose still present were converted to sorbitol. The mixture contained a total of approximately 71% of sorbitol, 28% of fructose, and 1% of glucose. In a further reaction step, 60 μl of NADH oxidase from *Leuconostoc mesenteroides* (overexpressed in *E. coli* BL21 (DE3), 350 U/ml) and 40 μl of sorbitol dehydrogenase from *Bacillus subtilis* (overexpressed in *E. coli* BL21 (DE3), 50 U/ml) were added. Again, the reaction took place in an open system in order to guarantee oxygen supply to the NADH oxidase reaction. The reaction vessel was shaken for 48 h at 25° C. (Eppendorf Thermomix®, 850 rpm). A mixture of 60% of D-fructose, 35.2% of D-sorbitol, and 4.7% of D-glucose was obtained.

EXAMPLE 2

Materials and Methods for the Conversion of D-Fructose to Furan Derivatives

Dehydration reactions of D-fructose to HMF were carried out under different reaction conditions, optionally as standard batch process under microwave-assisted heating or by continuous-flow conditions. Surprisingly, it was found that compared to known systems the use of NMP as solvent in the reaction in combination with homogeneous or heterogeneous catalysts results in higher yields, in the microwave-assisted method as well as under continuous-flow conditions.
Synthesis of $SiO_2$—$MgCl_2$
$SiO_2$—$MgCl_2$ was produced similarly to the protocol according to Yasuda et al. (Yasuda, M.; Nakamura, Y.; Matsumoto, J.; Yokoi, H. Shiragami, T. Bull. Chem. Soc. Jpn. 2011, 84, 416-418).
Synthesis of SILPs
The SILP catalyst was produced according to known protocols (Fu, S.-K.; Liu, S.-T. Synth. Commun 2006, 36, 2059-2067) using N-methyl-imidazol. For immobilisation, the ionic liquid obtained was mixed with 200 wt % of silica gel in dry chloroform (100 ml per 10 g $SiO_2$) and heated for 24 h to 70° C. The solid obtained was filtered off, washed with chloroform, and dried under reduced pressure. The silica gel obtained had a catalyst load of approximately 16 wt %.
General Conditions of Batch Reactions
If not stated otherwise, all batch reactions were carried out in a 4 ml screw-lid glass jar. Heating was carried out in suitable aluminium blocks to the desired temperature.
Microwave Reactions in the Batch Process
Microwave reactions in a batch process were carried out in a Biotage Initiator Sixty laboratory microwave equipped with an autosampler in order to allow sequential reactions. The absorption level was set to the maximum value, which automatically controls the maximum energy input at 400 W.
Stopped-Flow Microwave Reactions and Continuous-Flow Reactions
Stopped-flow reactions for optimising semi-continuous processes were carried out on a CEM® Discover System with CEM® Voyager Upgrade and via an external pressure sensor. For reactions in continuous processes, a cartridge-based reactor system X-Cube by ThalesNano®, equipped with a Gilson® GX-271 autosampler for automatic product collection, was used. Here, two quartz sand cartridges (Cat-Cart®, 70×4 mm) were incorporated as reactions zones.
Alternatively, a perfluoro alkoxy alkane capillary was used (PFA capillary, 0.8 mm inner diameter, 1.6 mm outer diameter), which was wound around a heatable aluminium cylinder. The substrates were added via a Shimadzu LC-10AD HPLC pump at the desired flow rate. Exact volumes (column 16.0 ml; dead volume before and after the column 1.0 ml each) were determined by monitoring defined flow rates of the pure solvent by means of a digital stop watch.
Analysis of the Reactions for Converting D-Fructose to Furan Derivatives
For a quantitative HPLC analysis, reaction samples (22 μl, if not stated otherwise) were diluted with deionised water to 1 ml. For reaction samples having different concentrations, dilution was adapted so that the maximum concentration did not exceed 2 mg/ml.
To this solution, 100 μL of 3-hydroxy benzyl alcohol were added as internal standard, followed by thorough mixing of the sample. Solid residues were separated by centrifugation (5 min, 20000 G) or filtration (Phenex PTFE, 4 mm, 0.2 μm). Quantification was based on the areas of the peaks in the RI spectrum compared to the internal standard.
The samples were analysed via HPLC on a Thermo Scientific® Surveyor Plus System or a Shimadzu® Nexera System, each equipped with a PDA Plus and RI detector. For separation, the stationary phase was an ion exchange column by Phenomenex® (Rezex RHM-Monosaccharide H+ (8%), 150×7.8 mm, built of a crosslinked matrix of sulfonated styrene and divinyl benzene, FE form), and the eluent consisted of water (HPLC grade) and 0.1% TFA (HPLC grade). The column temperature was kept constant at 85° C., optimising running time to 25 min Product quantification was carried out by means of an internal standard via integration of the RI signal. In addition, the wavelengths of 200 nm, 254 nm and 280 nm were recorded by PDA for further reaction analysis.
GP1—D-Fructose Dehydration in the Batch Process
In a standard reaction for reaction optimisation, 100 mg of D-fructose (0.56 mmol) and a desired amount of the respective catalyst were put into a glass vial and treated with 1 ml freshly distilled NMP. The solution/suspension obtained was heated to the selected temperature and allowed to react for the desired time.
GP2—D-Fructose Dehydration in the Microwave Batch Process
In a standard reaction for reaction optimisation, 100 mg of D-fructose (0.56 mmol) and the desired amount of the respective catalyst were added to a microwave vessel (0.5-2.0 ml). The vessel was equipped with a magnetic stirring bar, and 1 ml of NMP was added. The radiation intensity of the microwave was automatically set by a company-internal regulation algorithm in order to achieve the desired temperature. Quick cooling of the reaction vessel was achieved by blowing in pressurised air of at least 6 bar.

GP3—D-Fructose Dehydration in the Microwave Stopped-Flow Process

In a standard reaction for reaction optimisation, a D-fructose standard solution (1 ml; c=100 mg/ml in NMP) and hydrochloric acid (100 µl; c=1 mol/l) were added to a microwave vessel equipped with a magnetic stirring bar. After sealing the vial with a snap cap, the solution was heated for the desired time to the desired temperature. In order to achieve the fastest possible heating, the energy applied was set according to the following Table 1.

TABLE 1

Power settings of the microwave and associated temperatures

| Temperature | Power setting |
|---|---|
| 100° C. | 50 W |
| 125° C. | 65 W |
| 150° C. | 100 W |
| 180° C. | 125 W |
| 200° C. | 140 W |
| 220° C. | 160 W |

Quick cooling of the reaction vessel was achieved by blowing in pressurised air of at least 6 bar.

GP4—D-Fructose Dehydration in the Cartridge-Based Reactor System

In a standard reaction for reaction optimisation, a D-fructose standard solution (1 ml; c=100 mg/ml in NMP) was mixed with hydrochloric acid (c=1 mol/l) and pumped into the reaction system by a reagent pump. During the heating process, several preliminary samples were taken in order to monitor a stable temperature and a stable flow rate. The reaction temperatures selected were 150° C., 180° C. and 200° C., while the reaction pressure was regulated at 40 bar. Flow rates between 0.2 and 0.6 ml/min were selected. Reaction samples were taken at amounts of 2.5 ml and analysed.

EXAMPLE 3

Use of Sulphuric Acid as Catalyst for Dehydrating D-Fructose

Different temperatures, reaction times and acid concentrations were compared. The reaction was carried out according to "GP1" (Example 4). The catalyst used was either 100 µl of 1N sulphuric acid or 10 µl of concentrated sulphuric acid. The results are summarised in Table 1.

TABLE 1

Sulphuric acid as catalyst for dehydrating D-fructose

| Catalyst | Temperature | Reaction time | Fructose consumption | HMF yield | HMF selectivity | LS yield |
|---|---|---|---|---|---|---|
| 1N H$_2$SO$_4$ | 100° C. | 3 h | 69% | 45% | 65% | <1% |
| 1N H$_2$SO$_4$ | 120° C. | 4 h | 95% | 77% | 81% | <1% |
| 1N H$_2$SO$_4$ | 150° C. | 15 min | 98% | 88% | 90% | <1% |
| 1N H$_2$SO$_4$ | 180° C. | 10 min | 100% | 85% | 85% | <1% |
| H$_2$SO$_4$ conc. | 120° C. | 45 min | 98% | 85% | 90% | <1% |
| H$_2$SO$_4$ conc. | 150° C. | 10 min | 100% | 90% | 90% | <1% |
| H$_2$SO$_4$ conc. | 180° C. | 5 min | 100% | 82% | 82% | <1% |

No formation of black, insoluble polymers and humans was observed under the optimum conditions used.

EXAMPLE 4

Use of Sulphuric Acid for Catalysing the Conversion of D-Fructose to Furan Derivatives (Continuous Process)

D-fructose (10% w/v) and concentrated sulphuric acid (1% v/v) were dissolved in N-methyl-2-pyrrolidone. The mixture was pumped through the reactor by means of a PFA capillary with continuous flow (reaction temperature 150° C.). After the first 18 ml had been discarded, further 10 ml were collected for analysis. With various flow rates, the effect of different dwell times in the reactor were tested (Table 10).

TABLE 10

Sulphuric acid for catalysing the conversion of D-fructose to furan derivatives (continuous process)

| Flow rate (ml/min) | Dwell time | Fructose consumption | HMF yield | HMF selectivity | LS yield |
|---|---|---|---|---|---|
| 0.8 ml/min | 20 min | 100% | 74% | 74% | <1% |
| 1.6 ml/min | 10 min | 100% | 75% | 75% | <1% |
| 3.2 ml/min | 5 min | 100% | 76% | 76% | <1% |

No formation of black, insoluble polymers and humins was observed under the conditions analysed.

EXAMPLE 5

Use of Amberlite 15® as Catalyst for Dehydrating D-Fructose

This example shows the use of a strong ion exchanger with sulfonic acid residues based on a macro-crosslinked resin. 100 mg of D-fructose were incubated in the presence of 1 ml of N-methyl-2-pyrrolidone for 3 h at 100° C. under stirring (protocol GP1, Example 2). Amberlite 15® was added as catalyst. Table 2 shows the result of this experiment. A high yield was achieved at the relatively low temperature. The formation of tar-like compounds was avoided.

TABLE 2

Amberlite 15 ® as catalyst for dehydrating D-fructose

| Amount of catalyst | Temp. | Reaction time | Fructose consumption | HMF yield | HMF selectivity | LS yield |
|---|---|---|---|---|---|---|
| 10 mg | 100° C. | 3 h | 70% | 50% | 71% | <1% |

The invention claimed is:

1. A method for the production of D-fructose, comprising:
providing a mixture comprising D-glucose and D-fructose as a starting material;
isomerising D-glucose to D-fructose by reduction of D-glucose to D-sorbitol and subsequent oxidation of D-sorbitol to D-fructose using redox cofactors NAD$^+$/NADH and NADP$^+$/NADPH, wherein one of the redox cofactors is obtained in a reduced form and the other redox cofactor is obtained in an oxidised form as a result of at least two enzymatically catalysed redox reactions (product forming reactions) taking place in a one-pot reaction; and
in a regeneration reaction, regenerating the redox cofactors in the one-pot reaction, wherein a) in the regeneration reaction, which transfers the reduced cofactor back to its originally oxidised form, oxygen or a compound of the general formula

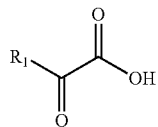

I wherein $R_1$ is a straight or branched $(C_{1-4})$-alkyl group or a $(C_{1-4})$-carboxyalkyl group, is reduced, and b) in the regeneration reaction, which transfers the oxidised cofactor back to its originally reduced form, a $(C_{4-8})$cycloalkanol or a compound of the general formula

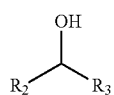

II wherein $R_2$ and $R_3$ are each independently selected from the group consisting of H, $(C_{1-6})$alkyl, wherein the alkyl is straight or branched, $(C_{2-6})$alkenyl, wherein the alkenyl is straight or branched and contains one to three double bonds, aryl, carboxyl, or $(C_{1-4})$carboxyalkyl, is oxidised.

2. The method according to claim 1, wherein in a) a compound of the general formula I, wherein $R_1$ is a substituted or unsubstituted $(C_{1-4})$alkyl group, is reduced, and in b) a compound of the general formula II, wherein $R_2$ and $R_3$ are independently selected from the group consisting of H, $(C_{1-6})$alkyl, wherein alkyl is straight or branched, $(C_{2-6})$alkenyl, wherein alkenyl is straight or branched and optionally contains up to three double bonds, cycloalkyl, aryl, $(C_{1-4})$carboxyalkyl, if compound I is a pyruvate, optionally also carboxyl, is oxidised.

3. The method according to claim 1, wherein in b) a compound of formula II, wherein $R_2$ and $R_3$ are independently selected from the group consisting of H, $(C_1-C_6)$ alkyl, wherein alkyl is straight or branched, $(C_{2-6})$alkenyl, wherein alkenyl is straight or branched and contains one to three double bonds, aryl, carboxyl, or $(C_{1-4})$carboxyalkyl, is oxidised.

4. The method according to claim 1, wherein the isomerisation of D-glucose to D-fructose follows the following reaction scheme 1:

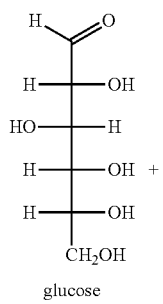

glucose

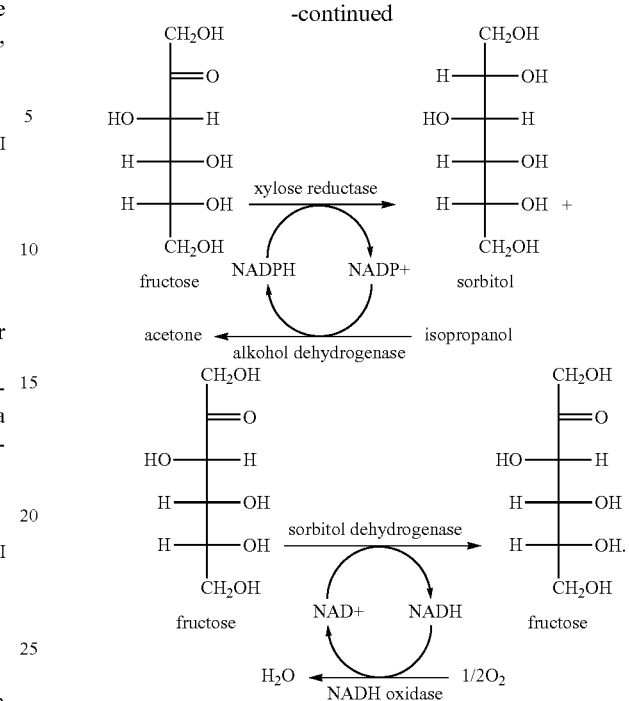

5. The method according to claim 1, wherein the oxidation reaction(s) and reduction reaction(s) take place parallel in time.

6. The method according to claim 1, wherein the oxidation reaction(s) and reduction reaction(s) do not take place parallel in time.

7. The method according to claim 1, wherein in the regeneration reaction, which transfers the oxidised cofactor $NAD(P)^+$ back to its originally reduced form $NAD(P)H$, 2-propanol is oxidised to acetone by means of an alcohol dehydrogenase.

8. The method according to claim 1, wherein in the regeneration reaction, which transfers the reduced cofactor $NAD(P)H$ back to its originally oxidised form $NAD(P)^+$, oxygen is reduced to water by means of an NADH oxidase.

9. The method according to claim 1, wherein the substrate(s) for the oxidation reaction(s) involved in the product formation is/are present in the one-pot reaction in a concentration of 5% (w/v) or more.

10. The method according to claim 1 wherein the fructose obtained according to claim 1 is isolated in a crystallised form.

11. The method according to claim 1, wherein at least one of $R_2$ or $R_3$ is selected from the group consisting of $(C_{6-12})$ aryl, $(C_{1-4})$carboxyalkyl, and $(C_{3-8})$cycloalkyl.

12. The method according to claim 1, wherein the substrate(s) for the oxidation reaction(s) involved in the product formation is/are present in the one-pot reaction in a concentration of 7% (w/v).

13. The method according to claim 1, wherein the substrate(s) for the oxidation reaction(s) involved in the product formation is/are present in the one-pot reaction in a concentration of 9% (w/v).

14. A method for obtaining furan derivatives from a mixture of glucose and fructose, comprising:
A) converting a mixture comprising D-glucose and D-fructose to D-fructose in an enzymatic method by use and regeneration of redox cofactors, wherein one of two redox cofactors is obtained in a reduced form and the other redox cofactor is obtained in an oxidised form as a result of at least two additional enzymatically catalysed redox reactions taking place in a one-pot reaction, wherein D-glucose is converted to D-fructose with the involvement of two or more oxidoreductases, and B) converting the D-fructose obtained in A) to furan derivatives.

15. The method according to claim 14, wherein in stage B) an acidic catalyst and a solvent are used.

16. The method according to claim 14, wherein the conversion of D-fructose to furan derivatives in stage B) is carried out as either a batch process or as a continuous process.

17. The method of claim 16, wherein the conversion of D-fructose to furan derivatives in stage B) is carried out under microwave heating.

18. The method according to claim 15, wherein during conversion of D-fructose to furan derivatives in stage B) the acidic catalyst used is a homogeneous acidic catalyst; a heterogeneous acidic catalyst a Lewis acid catalyst, a SILP catalyst.

19. The method according to claim 18, wherein the homogeneous acidic catalyst comprises at least one of sulphuric acid or hydrochloric acid.

20. The method according to claim 18, wherein the heterogeneous acidic catalyst comprises an ion exchanger.

21. The method according to claim 18, wherein the Lewis acid catalyst comprises at least one of $CrCl_2$, $AlCl_3$ or $SiO_2$—$MgCl_2$.

22. The method according to claim 14, wherein the furan derivative is hydroxyl methyl furfural of the following formula

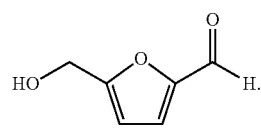

* * * * *